United States Patent [19]

Loo

[11] Patent Number: 5,334,688

[45] Date of Patent: Aug. 2, 1994

[54] FULLY SUBSTITUTED CYCLOPOLYSILOXANES AND THEIR USE FOR MAKING ORGANOSILICON POLYMERS

[75] Inventor: De-Kai Loo, Hockessin, Del.

[73] Assignee: Hercules Incorporated, Wilmington, Del.

[21] Appl. No.: 49,097

[22] Filed: Apr. 19, 1993

[51] Int. Cl.$^5$ ............................................. C08G 77/20
[52] U.S. Cl. ....................................... 528/15; 528/21; 528/24; 528/37
[58] Field of Search ........................ 528/15, 24, 37, 21

[56] References Cited

U.S. PATENT DOCUMENTS

| | | | |
|---|---|---|---|
| 3,197,432 | 7/1965 | Lamoreaux | 260/46.5 |
| 3,197,433 | 7/1965 | Lamoreaux | 260/46.5 |
| 3,438,936 | 4/1969 | Lamoreaux | 260/46.5 |
| 4,524,187 | 6/1985 | Greco et al. | 525/332.1 |
| 4,599,440 | 7/1986 | Watanabe et al. | 556/460 |
| 4,877,820 | 10/1989 | Cowan | 523/222 |
| 4,900,779 | 2/1990 | Leibfried | 524/862 |
| 4,902,731 | 2/1990 | Leibfried | 523/222 |
| 5,008,360 | 4/1991 | Bard et al. | 528/25 |
| 5,013,809 | 5/1991 | Leibfried, Sr. | 524/862 |
| 5,068,303 | 11/1991 | Bard et al. | 528/25 |

FOREIGN PATENT DOCUMENTS 294027 9/1991 German Democratic Rep. .

OTHER PUBLICATIONS

T. V. Chogovadze, et al.: "Hydrosilation Reaction of Dicyclopentadiene", Dokl. Akad. Nauk SSSR, 1979, 246(4), 891–5 (abstract from Chemical Abstracts).
"Phosphorus Based Catalyst Retardants for Silicon--Carbide Resin Systems", Research Disclosure, 326103, Jun. 1991.
W. Risse, et al.: "Di- and Tetrafunctional Initiators for the Living Ring-Opening Olefin Metathesis Polymerization of Strained Cyclic Olefins", Macromolecules, 22(8), 3205–3210, 1989.

Primary Examiner—Melvyn I. Marquis
Attorney, Agent, or Firm—Joanne W. Patterson

[57] ABSTRACT

Disclosed are organosilicon crosslinked polymers and crosslinkable prepolymers that are the reaction product of (a) a cyclic polysiloxane in which each silicon atom is substituted with (i) a saturated, substituted or unsubstituted alkyl or alkoxy group or a substituted or unsubstituded aryl or aryloxy group, and (ii) a substituted or unsubstituted hydrocarbon group having at least one carbon-carbon double bond that is reactive in hydrosilation, (b) at least one organosilicon compound having at least two ≡SiH groups, and optionally (c) a hydrocarbon polyene having at least two nonaromatic carbon-carbon double bonds that are reactive in hydrosilation. A process for preparing the polymers and prepolymers and for preparing the cyclic polysiloxanes is also disclosed.

20 Claims, No Drawings

FULLY SUBSTITUTED CYCLOPOLYSILOXANES AND THEIR USE FOR MAKING ORGANOSILICON POLYMERS

FIELD OF THE INVENTION

This invention relates to the preparation of organosilicon polymers and prepolymers from cyclic polysiloxanes. This invention also relates to the preparation of cyclic polysiloxanes.

BACKGROUND OF THE INVENTION

Leibfried, in U.S. Pat. Nos. 4,900,779, 4,902,731 and 5,013,809, and Bard and Burnier in U.S. Pat. Nos. 5,008,360 and 5,068,303, describe crosslinked organosilicon polymers and crosslinkable organosilicon prepolymers comprising alternating polycyclic hydrocarbon residues and cyclic polysiloxane or siloxysilane residues linked through carbon-to-silicon bonds. These polymers are useful, for example, in structural and electronic applications.

Although cyclic trisiloxanes were disclosed for use in the preparation of organosilicon polymers and prepolymers in U.S. Pat. No. 5,013,809 (Leibfried) and in *Research Disclosure* 326103 (June, 1991), these cyclic trisiloxanes were required to have two or more hydrogen atoms bound to silicon. Only cyclosiloxanes containing four or more silicon atoms were used in the preparation of these polymers and prepolymers, because cyclotrisiloxanes are not readily available and are unstable. It is also known that cyclotrisiloxanes with hydrogen atoms and methyl groups bonded to every silicon atom are not storage-stable.

Cyclopolysiloxanes in which some of the Si atoms are substituted with unsaturated polycyclic groups have been disclosed in U.S. Patent 4,599,440, e.g., the reaction product of pentamethylcyclotrisiloxane and 5-ethylidenebicyclo(2,2,1)hept-2-ene. None of these compounds have unsaturated hydrocarbon groups on every silicon atom.

SUMMARY OF THE INVENTION

The organosilicon crosslinked polymers or crosslinkable prepolymers of this invention are the hydrosilation reaction product of:

(a) a cyclic polysiloxane having the formula:

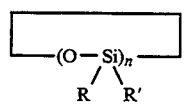

where R is a saturated, substituted or unsubstituted alkyl or alkoxy group or a substituted or unsubstituted aryl or aryloxy group, R' is a substituted or unsubstituted hydrocarbon group having at least one nonaromatic carbon-carbon double bond that is reactive in hydrosilation, and n is 3, or 3 and 4, and (b) at least one organosilicon compound having at least two ≡SiH groups selected from the group consisting of (1) cyclic polysiloxanes and (2) tetrahedral siloxysilanes.

The reaction mixture can optionally contain as a third component (c) at least one hydrocarbon polyene having at least two nonaromatic carbon-carbon double bonds that are reactive in hydrosilation.

The present invention also discloses a method for preparing fully-substituted cyclic polysiloxanes, and processes for preparing prepolymers and polymers from the fully-substituted cyclic polysiloxanes, other organosilicon compounds, and, optionally, a polycyclic polyene.

The organosilicon polymers of this invention have improved shear modulus and coefficient of thermal expansion compared with polymers made without the fully-substituted cyclic polysiloxanes. The invention also provides a simple method for preparing storage-stable cyclic polysiloxanes.

DETAILED DESCRIPTION OF THE INVENTION

The fully-substituted cyclic polysiloxanes used as component (a) in the preparation of the organosilicon polymers and prepolymers of this invention have the general formula:

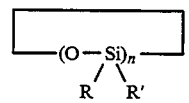

where R and R' are defined below and n=3, or 3 and 4. The notation "3 and 4" means that a mixture of a cyclic trisiloxane (n=3) and a cyclic tetrasiloxane (n=4) is used.

The fully-substituted cyclic polysiloxanes are prepared by first reacting a dichlorosilane having the formula Cl$_2$HSiR in which R is a saturated, substituted or unsubstituted alkyl or alkoxy group or a substituted or unsubstituted aryl or aryloxy group, with a substituted or unsubstituted hydrocarbon polyene having at least two nonaromatic carbon-carbon double bonds that are reactive in hydrosilation. The alkyl groups are preferably 1–10 carbon alkyl groups and the aryl groups are preferably 6–10 carbon aryl groups. The alkyl or aryl groups of the dichlorosilane, or the hydrocarbon polyene, can be substituted with any substituents that do not interfere with subsequent hydrosilation reactions. Examples of suitable hydrocarbon polyenes include polycyclic polyenes such as, for example, cyclopentadiene oligomers (e.g., dicyclopentadiene, tricyclopentadiene and tetracyclopentadiene), bicycloheptadiene (also known as norbornadiene) and its Dieis-Alder oligomers with cyclopentadiene (e.g., dimethanohexahydronaphthalene), norbornadiene dimer, hexahydronaphthalene, and substituted derivatives of any of these, e.g., methyldicyclopentadiene. Other hydrocarbon polyenes such as those containing a single carbocyclic ring, e.g., divinylbenzene and divinylcyclohexane, or an acyclic polyene such as isoprene can also be used. The preferred hydrocarbon polyenes are dicyclopentadiene (DCPD) and norbornadiene.

The reaction of the dichlorosilane and the hydrocarbon polyene is carried out in the presence of a hydrosilation catalyst. Hydrosilation catalysts include those compounds discussed below in relation to the preparation of organosilicon polymers and prepolymers. In this reaction one of the carbon-carbon double bonds of the hydrocarbon polyene reacts with the ≡SiH group of the dichlorosilane, and the remaining double bond is unreacted.

The product of this hydrosilation reaction is RCl$_2$SiR', where R' is a substituted or unsubstituted hydrocarbon group having at least one nonaromatic carbon-carbon double bond that is reactive in hydrosilation, which is derived from the hydrocarbon polyene. RCl₂SiR' is then cyclized by one of three methods to produce the cyclic polysiloxanes of this invention: (1) direct hydrolysis, for example, in ether or methyl ethyl ketone, (2) reaction with a secondary or tertiary alcohol and (3) oxidation with a metal oxide.

Method (1) is preferred for cyclizing $RCl_2SiR'$ compounds where R' is derived from dicyclopentadiene.

Suitable tertiary alcohols for use in method (2) include, for example, 2-methylbutan-2-ol, 3-methylpentan-3-ol, 3-ethylpentan-3-ol and t-butyl alcohol. Suitable secondary alcohols include, for example, 2-propanol, 2-butanol, 2-pentanol, 3-pentanol and 3,3-dimethylbutan-2-ol. Tertiary alcohols are preferred. t-Butyl alcohol is most preferred.

Metal oxides preferred for use in method (3) include, for example, ZnO, MgO and CuO. Zinc oxide is most preferred. Reaction with ZnO is preferred for $RCl_2SiR'$ compounds where R' is derived from norbornadiene, and for compounds where R is an alkoxy or aryloxy group.

The preparation of the fully substituted cyclic polysiloxanes can be summarized as follows, using the pure cyclic trisiloxane as an example.

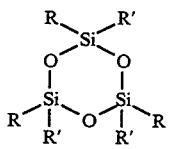

where R is a saturated, substituted or unsubstituted alkyl or alkoxy group or a substituted or unsubstituted aryl or aryloxy group, and R' is a substituted or unsubstituted hydrocarbon group having at least one nonaromatic carbon-carbon double bond that is reactive in hydrosilation.

Pure cyclic trisiloxane can be obtained by standard processing techniques. However, 10% to 46% of the cyclic tetrasiloxane having the formula:

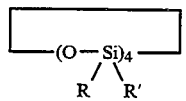

where R and R' are the same as above, is typically also present in the cyclic polysiloxane reaction product. The amount of the cyclic tetrasiloxane present depends upon the synthesis method, reaction conditions and solvent used and on the size of the groups R and R' in the molecule. For example, when R' is derived from dicyclopentadiene, a smaller percentage of the cyclic tetrasiloxane is present when $RCl_2SiR'$ is reacted with t-butyl alcohol than when $RCl_2SiR'$ is hydrolyzed in methyl ethyl ketone. When $RCl_2SiR'$ is reacted with ZnO, a smaller percentage of the cyclic tetrasiloxane is obtained when R' is derived from dicyclopentadiene than when R' is derived from norbornadiene. The mixture of the cyclic trisiloxane and the cyclic tetrasiloxane can also be used in preparing the polymers and prepolymers of this invention.

Any cyclic polysiloxane or tetrahedral siloxysilane with two or more hydrogen atoms bound to silicon can be used as component (b) in the preparation of the organosilicon polymers or prepolymers of this invention. The cyclic polysiloxanes have the general formula:

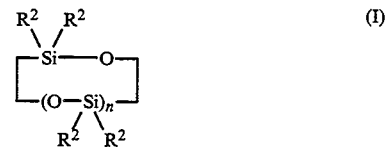

wherein $R^2$ is hydrogen, a saturated, substituted or unsubstituted alkyl or alkoxy group, a substituted or unsubstituted aryl or aryloxy group, n is an integer from 2 to 20, and $R^2$ is hydrogen on at least two of the silicon atoms in the molecule.

Suitable cyclic polysiloxane compounds include those disclosed in U.S. Pat. Nos. 4,900,779; 4,902,731; 5,013,809; 5,077,134; 5,008,360; 5,068,303; and 5,025,048, all of which are incorporated by reference in their entirety. Examples of reactants of Formula (I) include, for example, trimethylcyclotrisiloxane, tetraoctylcyclotetrasiloxane, and hexamethylcyclotetrasiloxane; tetra- and pentamethylcyclotetrasiloxanes; tetra-, penta-, hexa- and heptamethycyclopentasiloxanes; tetra-, penta- and hexamethylcyclohexasiloxanes, tetraethylcyclotetrasiloxanes and tetraphenylcyclotetrasiloxanes.

Preferred cyclic polysiloxanes are the methylhydrocyclosiloxanes, for example, 1,3,5,7-tetramethylcyclotetrasiloxane; 1,3,5,7,9-pentamethylcyclopentasiloxane and 1,3,5,6,9,11-hexamethylcyclohexasiloxane, or mixtures thereof. In most cases, a mixture of a number of these species is used, wherein n can vary widely. Reference to "methylhydrocyclosiloxanes" is intended to refer to such mixtures.

The tetrahedral siloxysilanes are represented by the structural formula:

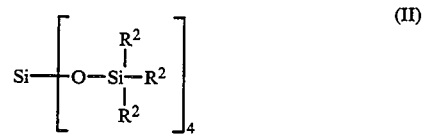

wherein $R^2$ is as defined above and is hydrogen on at least two of the silicon atoms in the molecule.

Examples of reactants of Formula (II) include, e.g., tetrakisdimethylsiloxysilane, tetrakisdiphenylsiloxysilane, and tetrakisdiethylsiloxysilane. Tetrakisdimethylsiloxysilane is the best known and preferred species in this group.

The hydrocarbon polyenes that can be used as optional component (c) in preparing the polymers and prepolymers of this invention are hydrocarbon polyenes having at least two nonaromatic carbon-carbon double bonds that are reactive in hydrosilation. Preferably the polyenes are polycyclic polyenes where the double bonds are in the rings of the compounds. Suitable compounds include for example, cyclopentadiene oligomers (e.g., dicyclopentadiene, tricyclopentadiene and tetracyclopentadiene), norbornadiene dimer, bicycloheptadiene (i.e., norbornadiene) and its Diels-Alder oligomers with cyclopentadiene (e.g., dimethanohexahydronaphthalene), and substituted derivatives of any of these, e.g., methyldicyclopentadiene. Preferred are cyclopentadiene oligomers such as dicyclopentadiene and tricyclopentadiene, with dicyclopentadiene being most preferred. Two or more hydrocarbon polyenes can be used in combination.

Other hydrocarbon compounds can also be used. For instance, according to one embodiment described in U.S. Pat. No. 5,008,360, which is incorporated by reference in its entirety, the hydrocarbon component comprises at least one low molecular weight (typically having a molecular weight less than 1,000, preferably less than 500) polyene having at least two nonaromatic carbon-carbon double bonds highly reactive in hydrosilation. The polyene can contain other less reactive (including unreactive) double-bonds, provided that those double bonds do not interfere with the reactivity of the highly reactive double bonds. Compounds having only two highly reactive double bonds are preferred. The carbon-carbon double bonds can be either in an alpha, beta or gamma position on a linear carbon moiety, next to two bridgehead positions in a strained polycyclic aliphatic ring structure, or in a cyclobutene ring. Examples include 5-vinyl-2-norbornene; o-, m- or p-diisopropenylbenzene; o-, m- or p-divinylbenzene, diallyl ether, diallylbenzene, dimethanohexahydronaphthalene and the symmetrical isomer of tricyclopentadiene.

The reactions for forming the organosilicon polymers and prepolymers of this invention are described in U.S. Pat. Nos. 4,900,779; 4,902,731; 5,013,809; 5,077,134; 5,008,360; 5,068,303; 5,025,048; and 4,877,820, each of which is incorporated by reference in its entirety.

When components (a) and (b), or (a), (b) and (c) are used to prepare the polymer or prepolymer, a mixture of all the components can be reacted in the presence of a catalyst. Alternatively, component (b), the silicon compound having at least two ≡SiH groups, and (c), the hydrocarbon polyene, are reacted in the presence of a catalyst to form an intermediate product, and the intermediate product is then reacted with (a), the fully substituted cyclic polysiloxane, in the presence of additional catalyst. Alternatively (a) the fully substituted cyclic polysiloxane and (b) the silicon compound having at least two ≡SiH groups, are reacted in the presence of a catalyst to form an intermediate product, and the intermediate product is then reacted with (c) the hydrocarbon polyene, in the presence of additional catalyst.

The reactions for forming the polymers and prepolymers of this invention can be promoted thermally or by the addition of a hydrosilation catalyst or a free radical generator such as a peroxide or an azo compound. Hydrosilation catalysts include metal salts and complexes of Group VIII elements. The preferred hydrosilation catalysts contain platinum, e.g., bis(acetonitrile)-platinum dichloride, his (benzonitrile) platinum dichloride, platinum on carbon, platinum dichloride, platinum-divinyl complexes, cyclooctadieneplatinum dichloride, dicyclopentadieneplatinum dichloride and chloroplatinic acid. The platinum catalyst is present in an amount of 0.0005% to 0.05% by weight of platinum, based on the weight of the monomers, preferably 0.002% to 0.05%, and most preferably 0.005% to 0.01%.

It is possible, by selection of reactants, reactant concentrations and reaction conditions, to prepare polymers exhibiting a broad range of properties and physical forms. Thus, it has been found possible to prepare tacky solids, elastomeric materials, and tough glassy polymers.

Generally, the ratio of carbon-carbon double bonds in the fully substituted cyclic polysiloxane or mixtures thereof with the hydrocarbon polyene, to ≡SiH groups in the organosilicon compounds is in the range of 0.5:1 to 1.3:1, preferably 0.7:1 to 1.1:1, most preferably 0.95:1 to 1.05:1.

The prepolymers are stable at room temperature for varying periods of time, and cure upon reheating to an appropriate temperature, e.g., about 100° to about 250° C. Frequently additional catalyst is added to the prepolymer prior to cure to further promote the reaction.

When preparing the polymers and prepolymers of this invention, the reaction speed and its accompanying viscosity increase can be controlled by use of low levels of a cure rate retardant (complexing agent), such as N,N,N',N'-tetramethylethylenediamine, diethylenetriamine or phosphorus compounds, such as those described in "Phosphorus Based Catalyst Retardants for Silicon Carbon Resin Systems", *Research Disclosure* 326103 (June 1991), which is incorporated by reference in its entirety. The cure rate retardants are also useful to maintain the storage stability and to control the viscosity profile of the prepolymer as described in European Patent Application 479,310 (Babcock et al.), which is incorporated by reference in its entirety.

Stabilizers (antioxidants) are useful to maintain storage stability and thermal oxidative stability. Suitable stabilizers include, for example, bis(1,2,2,6,6-pentamethyl-4-piperidinyl)-(3,5-di-tert-butyl-4-hydroxybenzyl)-butylpropanedioate (available as TINUVIN ™ 144 from Ciba-Geigy Corp., Hawthorne, N.Y.), or a combination of octadecyl 3,5-di-tert-butyl-4-hydroxyhydrocinnamate (also known as octadecyl 3-(3',5'-di-tert-butyl-4'-hydroxyphenyl)propionate ) available as NAUGARD ™ 76 from Uniroyal Chemical Co., Middlebury, Conn., and bis (1,2,2,6,6-pentamethyl-4-piperidinyl sebacate), available as TINUVIN ™ 765 from Ciba-Geigy Corp. Stabilizers and their use are described in U.S. Pat. Nos. 5,025,048 and 5,118,735, which are both incorporated by reference in their entirety.

An elastomer can be added to improve the toughness of the organosilicon polymer-containing compositions of the present invention. Although any elastomer can be added to impart toughness, hydrocarbon elastomers are preferred for use in the present invention. Preferred are ethylenepropylene-ethylidenenorbornene polymers having a molecular weight of from about 5500 to about 7000. Elastomers are generally used in an amount of from about 0.5 to 20 weight %, preferably from about 3 to about 12 weight % of the total composition. Elastomers can be added to the monomers or to the prepolymer. Use of elastomers is described in U.S. Pat. No. 5,147,958 and European Patent Application 482,404 (Barnum & Brady), as well as "Organosilicon Compositions Containing Hydrocarbon Elastomers", *Research Disclosure* 33082 (October 1991), all of which are incorporated by reference in their entirety.

One or more flame retardants can also be added to the compositions of this invention. The flame retardant preferably comprises at least one member selected from the group consisting of phosphorus-containing compounds and halogen-containing compounds. Exemplary are ammonium polyphosphates, phosphazenes, phosphine oxides, phosphate esters, elemental red phosphorus, brominated alkyls, brominated diphenyl oxides, brominated polystyrenes, brominated bisphenol A's, and hexachlorocyclopentadiene derivatives. Use of flame retardants is described in U.S. Ser. No. 07/839,610 (Babcock et al.), filed Feb. 2, 1992, which is incorporated by reference in its entirety.

Fillers can also be added to the compositions of this invention. Typical fillers include, for example, carbon black, vermiculite, mica, wollastonite, calcium carbonate, sand, glass spheres, glass beads, ground glass, waste glass, fused silica, fumed silica, synthetic silica, glass fibers, and glass flakes. Other useful fillers include the fiber reinforcements that are described in U.S. Pat. Nos. 4,900,779, 4,902,731, 5,008,360 and 5,068,303, each of which is incorporated herein by reference.

The polymers and prepolymers of this invention have excellent electrical insulating properties and resistance to moisture. They are therefore well suited for electronic applications, e.g., composites, adhesives, encapsulants, potting compounds and coatings. They are especially useful in applications requiring high shear modulus, low coefficient of thermal expansion and moderate glass transition temperature, for example, in the manufacture of printed circuit boards and high performance composites.

All parts and percentages in this specification are by weight unless otherwise noted.

EXAMPLE 1

This example describes the preparation of a fully substituted cyclotrisiloxane in which cyclization occurs after hydrolysis of the R'-substituted dichlorosilane in methyl ethyl ketone.

Dicyclopentadiene (DCPD) (200 g, 1.52 mol) and 2,332 μl (2.06 μl=10 ppm/g resin, 30 ppm) of a platinum-divinyl complex (a vinyl-terminated polydimethylsiloxane/toluene solution supplied by Huls American), were added to a three-necked 500 ml round bottom flask equipped with a condenser and a dropping funnel. Dichloromethylsilane (177.4 g, 1.54 mol) was added dropwise through the dropping funnel at room temperature with a magnetic stirrer. An exothermic reaction (2° C. increase) was observed. After addition, the temperature was raised to 45°–50° C. and this temperature was maintained for three hours. The reaction mixture was cooled to room temperature. Vacuum distillation of the mixture was carried out using a Kugelrohr apparatus. The product, methyl (2,3-dihydro-2-dicyclopentadienyl)-dichlorosilane (312.3 g, 82.8%), was collected between 80° and 100° C. at a vacuum of 1 mm Hg.

An aqueous solution of methyl ethyl ketone (MEK) (7 g water in 150 ml MEK) was placed in a three-necked flask equipped with a condenser and a dropping funnel. Methyl (2,3-dihydro-2-dicyclopentadienyl)-dichlorosilane (40 g, 0.16 mol) was added through the dropping funnel. After addition, the solution was refluxed for two hours. The residue was dissolved in ether and washed with saturated sodium bicarbonate solution (100 ml) and distilled water (150 ml×4). The solution was dried over anhydrous magnesium sulfate. The solvent was then evaporated in vacuo, first by a Rotovap, then by a Kugelrohr distillation apparatus at 80° C. under a vacuum of 1 mm Hg. A mixture of the fully substituted cyclic trisiloxane (1,3,5-tris(2,3-dihydro-2-dicyclopentadienyl)-1,3,5-trimethylcyclotrisiloxane) and the corresponding fully substituted cyclic tetrasiloxane was obtained at 96% yield (30.0 g). The product was a colorless viscous oil, which turned to a white solid on standing. The ratio of cyclic trisiloxane to cyclic tetrasiloxane was 54/46 mol %.

EXAMPLE 2

This example describes the preparation of a fully substituted cyclotrisiloxane in which cyclization occurs after hydrolysis of the R'-substituted dichlorosilane in aqueous ether.

Methyl (2,3-dihydro-2-dicyclopentadienyl)dichlorosilane (38.0 g, 0.15 mol), prepared as described in Example 1, was added through a dropping funnel to an aqueous solution of ether (8 ml of water in 150 ml of ether). After addition, the solution was refluxed for four hours. The solution was cooled to room temperature and washed with distilled water (100 ml), saturated sodium bicarbonate (100 ml), and distilled water (100 ml×4) in sequence. The organic layer was dried over anhydrous magnesium sulfate. The solvent was evaporated in vacuo. The product was a colorless viscous oil, which turned to a white solid on standing. A mixture of fully substituted cyclic trisiloxane (1,3,5-trimethylcyclotrisiloxane) and the corresponding fully substituted cyclic tetrasiloxane was obtained at 95% yield (28.0 g). The ratio of cyclic trisiloxane to cyclic tetrasiloxane was 90/10 mol %.

EXAMPLE 3

This example describes the preparation of a fully substituted cyclotrisiloxane in which cyclization occurs after reaction of the R'-substituted dichlorosilane with t-butyl alcohol.

A solution of 32.0 g (0.44 mol) of t-butyl alcohol in 120 ml of hexane was added to a three-necked flask equipped with a condenser and a dropping funnel. Methyl (2,3-dihydro-2-dicyclopentadienyl) dichlorosilane (50 g, 0.20 mol), prepared as described in Example 1, was added through the dropping funnel. The reaction temperature was controlled below 15° C. by an external ice bath and by the rate of addition. The solution was washed with saturated sodium bicarbonate solution (100 ml) and distilled water (100 ml×5) and then dried over anhydrous magnesium sulfate. The solvent was evaporated in vacuo using a rotoevaporator and a Kugelrohr distillation apparatus in sequence. A mixture of the fully substituted cyclic trisiloxane (1,3,5-tris(2,3-dihydro-2-dicyclopentadienyl)-1,3,5-trimethylcyclotrisiloxane) and the corresponding fully substituted cyclic tetrasiloxane was obtained at 75% yield (28.8 g). The product was a white solid. The ratio of cyclic trisiloxane to cyclic tetrasiloxane was 65/35 mol %.

EXAMPLE 4

This example describes the preparation of a fully substituted cyclotrisiloxane in which cyclization occurs after reaction of the R'-substituted dichlorosilane with ZnO in ethyl acetate.

Bicyclo[2.2.1]heptenylmethyldichlorosilane was prepared by the method described in Example 1, using norbornadiene instead of dicyclopentadiene.

Bicyclo[2.2.1]heptenylmethyldichlorosilane (30.0 g, 0.12 mole) was added dropwise to a mixture of 11.9 g (0.145 mole) of zinc oxide and 100 ml of ethyl acetate at room temperature under a nitrogen atmosphere with agitation. The mixture was heated to reflux for five hours. The mixture was cooled to room temperature and the white solid was filtered off through CELITE ™ filter aid supplied by Manville Corp. The organic solution was washed with brine (1×100 ml), saturated sodium bicarbonate (1×100 mol), and brine (3×100 ml) respectively. The solution was then dried over anhydrous magnesium sulfate and the solvent was evaporated under vacuum. A mixture of the fully substituted cyclic trisiloxane (1,3,5-trimethyl-1,3,5-trikis[5-bicyclo(2.2.1)heptenyl]cyclotrisiloxane) and the corresponding fully substituted cyclic tetrasiloxane was obtained at 81% yield (18.5 g). The product was a viscous liquid, which turned to a white solid on standing. The ratio of cyclic trisiloxane to cyclic tetrasiloxane was 60/40 mol %.

COMPARATIVE EXAMPLE 1

This example describes the preparation of a prepolymer and cured polymer from a polycyclic polyene and a methylhydrocyclosiloxane without a fully substituted cyclic polysiloxane.

Dicyclopentadiene (11.0 g), 10.4 g of 1,3,5,7-tetramethylcyclotetrasiloxane (Huls American), and 0.15 ml of a platinum-divinyl complex (Huls American PCO72, a xylene solution containing 0.56% of Pt, 35 ppm) were added to a round bottom one-neck flask. Heating the mixture to 70° C. resulted in an exothermic reaction and formation of an organosilicon prepolymer. To this prepolymer was added 0.33 ml of PCO72 (75 ppm) in portions, followed by 8.4 ml of a solution of diethylenetriamine cure rate retardant (DETA) (5% in toluene, 20 ppm). The solvent was evaporated under vacuum. The catalyzed prepolymer was then poured into a mold. The sample was cured at 170° C. for one hour and postcured at 240° C. for four hours. The cured sample was a colorless and hazy solid. The shear modulus G' of the polymer was $8.80 \times 10^9$ dyne/cm$^2$ and was determined by dynamic mechanical analysis using a Rheometrics mechanical spectrometer Model RMS-605. The coefficient of thermal expansion (CTE) of the polymer was 95.8 ppm/° C. between 60° to 100° C. and was determined by thermal mechanical analysis (TMA) using a DuPont TMA Analyzer Model 220 (see Table 1).

EXAMPLE 5

This example describes the preparation of a prepolymer in which a polycyclic polyene was first reacted with a methylhydrocyclosiloxane in the presence of a catalyst and the reaction product was then reacted with a fully substituted cyclic polysiloxane in the presence of additional catalyst.

Dicyclopentadiene (6.1 g), 10.95 g of 1,3,5,7-tetramethylcyclotetrasiloxane, and 0.12 ml of a platinum-divinyl complex (Huls American PCO75, a vinyl-terminated polydimethylsiloxane/toluene solution containing 0.56% of Pt, 35 ppm) were added to a round bottom one-necked flask. Heating the mixture to 70° C. resulted in an exothermic reaction and formation of an organosilicon prepolymer. 1,3,5-Tris(2,3-dihydro-2-dicyclopentadienyl)-1,3,5-trimethylcyclotrisiloxane (17.4 g) in 20 ml of toluene was added to the prepolymer, followed by 0.65 ml of the platinum catalyst (total 110 ppm). The solvent was evaporated under vacuum and the catalyzed prepolymer was poured into a mold. The sample was cured at 170° C. for one hour and postcured at 240° C. for four hours. The cured sample was a colorless and hazy solid. The shear modulus of the polymer was $1.10 \times 10^{10}$ dyne/cm$^2$ by dynamic mechanical analysis. The CTE of the polymer was 91.6 ppm/° C. between 60° to 100° C. (TMA) (see Table 1).

COMPARATIVE EXAMPLE 2

This example describes the preparation of a prepolymer and cured polymer from dicyclopentadiene and a methylhydrocyclosiloxane without the use of a fully substituted cyclic polysiloxane.

Dicyclopentadiene (11.0 g), 10.0 g of 1,3,5,7-tetramethylcyclotetrasiloxane (Huls American), and 0.13 ml of a platinum-divinyl complex (Huls American PCO72, a xylene solution containing 0.56% of Pt, 30 ppm) were added to a round bottom one-neck flask. Heating the mixture to 70° C. resulted in an exothermic reaction and formation of an organosilicon prepolymer. To this prepolymer was added 0.30 ml of PCO72 (70 ppm) in portions, followed by 8.4 ml of a solution of diethylenetriamine cure rate retardant (DETA) (5% in toluene, 20 ppm). The solvent was evaporated under vacuum and the catalyzed prepolymer was poured into a mold. The sample was cured at 170° C. for one hour and postcured at 240° C. for four hours. The cured sample was a colorless and hazy solid. The shear modulus G' of the polymer was $8.20 \times 10^9$ dyne/cm$^2$ by dynamic mechanical analysis. The coefficient of thermal expansion (CTE) of the polymer was 102 ppm/° C. between 60° C. to 100° C. (TMA) (see Table 1).

EXAMPLE 6

This example describes the preparation of a prepolymer and cured polymer in which all of the components were added at the same time.

Dicyclopentadiene (40 g), 7.5 g of 1,3,5,7-tetramethylcyclotetrasiloxane, 11.6 g of 1,3,5-tris(2,3-dihydro-2-dicyclopentadienyl)-1,3,5-trimethylcyclotrisiloxane, and 0.14 ml of a platinum-divinyl complex (Huls American PCO75, a vinyl-terminated polydimethylsiloxane/toluene solution containing 0.56% of Pt, 30 ppm) were added to a round bottom one-necked flask. Heating the mixture to 70° C. resulted in an exothermic reaction and the formation of an organosilicon prepolymer. The same platinum catalyst (0.33 ml, 100 ppm) was added to the prepolymer. The solvent was evaporated under vacuum and the catalyzed prepolymer was poured into a mold. The sample was cured at 170° C. for one hour and postcured at 240° C. for four hours. The cured sample was a colorless and hazy solid. The shear modulus of the polymer was $1.11 \times 10^{10}$ dyne/cm$^2$ by dynamic mechanical analysis. The CTE of the polymer was 97.9 ppm/° C. between 60° C. to 100° C. (TMA) (see Table 1).

The data from Comparative Examples 1 and 2 and Examples 5 and 6 are summarized in the following table. The data indicate that the shear modulus G' increases and the coefficient of thermal expansion (CTE) decreases for cured polymers made from fully substituted cyclic polysiloxanes compared with polymers made without them.

TABLE 1

| Example | DCPD/D$_3$ (weight ratio) | PCO75 (ppm) | G' ($\times 10^9$) (dynes/cm$^2$) | CTE, ppm (60–100° C.) |
|---|---|---|---|---|
| Comp. Ex. 1 | 1/0 | 110 | 8.80 | 95.8 |
| Ex. 5 | 1/3 | 110 | 11.0 | 91.6 |
| Comp. Ex. 2 | 1/0 | 100 | 8.2 | 102.0 |
| Ex. 6 | 1/3 | 100 | 11.1 | 97.9 |

I claim:

1. An organosilicon crosslinked polymer or crosslinkable prepolymer that is the hydrosilation reaction product of:

(a) a cyclic polysiloxane having the formula

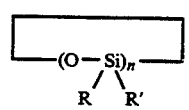

where R is saturated, substituted or unsubstituted alkyl or alkoxy group or a substituted or unsubstituted aryl or aryloxy group, R' is a substituted or unsubstituted hydrocarbon group having at least one nonaromatic carbon-carbon double bond that is reactive in hydrosilation, and n is 3, or 3 and 4, and (b) at least one organosilicon compound having at least two ≡SiH groups selected from the group consisting of (1) cyclic polysiloxanes and (2) tetrahedral siloxysilanes, said hydrosilation reaction being carried out in the presence of a hydrosilation catalyst.

2. The polymer or prepolymer of claim 1, wherein R' is a hydrocarbon group containing one carbocyclic ring or a polycyclic hydrocarbon group.

3. The polymer or prepolymer of claim 2, wherein R' is a polycyclic hydrocarbon group.

4. The polisher or prepolymer of claim 3, wherein the polycyclic hydrocarbon group is derived from a polycyclic polyene selected from the group consisting of cyclopentadiene oligomers, bicycloheptadiene and its Diels-Alder oligomers with cyclopentadiene, norbornadiene dimer, and hexahydronaphthalene.

5. The polymer or prepolymer of claim 4, wherein the polycyclic polyene is selected from the group consisting of dicyclopentadiene, tricyclopentadiene, tetracyclopentadiene, dimethanohexahydronaphthalene and methyldicyclopentadiene.

6. The polymer or prepolymer of claim 3, wherein R is a 1–10 carbon alkyl group.

7. The polymer or prepolymer of claim 6, wherein R is methyl and R' is a dicyclopentadienyl group.

8. The polymer or prepolymer of claim 6, wherein R is methyl and R' is a 5-bicyclo[2.2.1]heptenyl group.

9. The polymer or prepolymer of claim 1, wherein the cyclic polysiloxane of component (b) has the formula

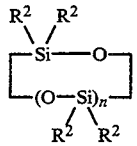

where $R^2$ is hydrogen, a saturated, substituted or unsubstituted alkyl or alkoxy group, or a substituted or unsubstituted aryl or aryloxy group, n is an integer from 2 to 20, and $R^2$ is hydrogen on at least two of the silicon atoms in the molecule.

10. The polymer or prepolymer of claim 9, wherein the cyclic polysiloxane of component (b) is selected from the group consisting of trimethylcyclotrisiloxane, tetraoctylcyclotetrasiloxane, hexamethylcyclotetrasiloxane; tetra- and pentamethylcyclotetrasiloxanes; tetra- penta-, hexa- and heptamethylcyclopentasiloxanes; tetra-, penta-, and hexamethylcyclohexasiloxanes, tetraethylcyclotetrasiloxanes and tetraphenylcyclotetrasiloxanes.

11. The polymer or prepolymer of claim 10, wherein the cyclic polysiloxane of component (b) is selected from the group consisting of 1,3,5,7-tetramethylcyclotetrasiloxane; 1,3,5,7,9-pentamethylcyclopentasiloxane; 1,3,5,6,9,11-hexamethylcyclohexasiloxane and mixtures thereof.

12. The polymer or prepolymer of claim 1, wherein the tetrahedral siloxysilane of component (b) has the formula

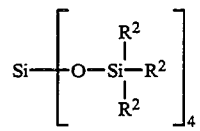

where $R^2$ is hydrogen, a saturated, substituted or unsubstituted alkyl or alkoxy group or a substituted or unsubstituted aryl or aryloxy group, and is hydrogen on at least two of the silicon atoms in the molecule.

13. The polymer or prepolymer of claim 12, wherein the tetrahedral siloxysilane is selected from the group consisting of tetrakisdiphenylsiloxysilane, tetrakisdiethylsiloxysilane and tetrakisdimethylsiloxysilane.

14. The polymer or prepolymer of claim 1, wherein R is a 1–10 carbon alkyl group.

15. The polymer or prepolymer of claim 1, wherein R is a 6–10 carbon aryl group.

16. The polymer or prepolymer of claim 6, wherein R in component (a) is methyl and R' is a dicyclopentadienyl or a 5-bicyclo[2.2.1]heptenyl group, and (b) is a cyclic polysiloxane selected from the group consisting of 1,3,5,7-tetramethylcyclotetrasiloxane; 1,3,5,7,9-pentamethylcyclopentasiloxane; 1,3,5,6,9,11-hexamethylcyclohexasiloxane and mixtures thereof.

17. A process for preparing a crosslinked polymer or a crosslinkable prepolymer comprising reacting:

(a) a cyclic polysiloxane having the formula

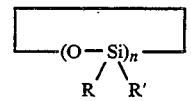

where R is a saturated, substituted or unsubstituted alkyl or alkoxy group or a substituted or unsubstituted aryl or aryloxy group, R' is a substituted or unsubstituted hydrocarbon group having at least one nonaromatic carbon-carbon double bond that is reactive in hydrosilation, and n is 3, or 3 and 4, and (b) at least one organosilicon compound having at least two ≡SiH groups selected from the group consisting of (1) (1) cyclic polysiloxanes and (2) tetrahedral siloxysilanes, in the presence of a hydrosilation catalyst.

18. The process of claim 17, wherein R in component (a) is a 1–10 carbon alkyl group, and R' is a polycyclic hydrocarbon group having at least one carbon-carbon double bond that is reactive in hydrosilation, and (b) is a cyclic polysiloxane.

19. The process of claim 18, wherein R in component (a) is a methyl group, R' is a dicyclopentadienyl group or a 5-bicyclo[2.2.1]heptenyl group, and (b) is a cyclic polysiloxane selected from the group consisting of 1,3,5,7-tetramethylcyclotetrasiloxane; 1,3,5,7,9-pentamethylcyclopentasiloxane; 1,3,5,6,9,11-hexamethylcyclohexasiloxane and mixtures thereof.

20. The process of claim 17, wherein the ratio of carbon-carbon double bonds in (a) to ≡SiH groups in (b) is 0.7:1 to 1:1.

* * * * *

UNITED STATES PATENT AND TRADEMARK OFFICE
CERTIFICATE OF CORRECTION

PATENT NO. : 5,334,688

DATED : August 2, 1994

INVENTOR(S) : De-Kai Loo

It is certified that error appears in the above-identified patent and that said Letters Patent is hereby corrected as shown below:

Column 11,
In claim 4, line 1, "polisher" should read --polymer--.

Column 12,
In claim 17, line 47, delete the second occurrence of "(1)".

Signed and Sealed this

Eighth Day of November, 1994

Attest:

BRUCE LEHMAN

Attesting Officer     Commissioner of Patents and Trademarks